United States Patent [19]
Vernon

[11] Patent Number: 5,976,506
[45] Date of Patent: *Nov. 2, 1999

[54] ORAL COMPOSITIONS

[75] Inventor: Peter George Vernon, Melton Mowbray, United Kingdom

[73] Assignee: Chesebrough-Pond's USA Co., Greenwich, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,548

[22] PCT Filed: Sep. 20, 1995

[86] PCT No.: PCT/EP95/03698

§ 371 Date: May 13, 1997

§ 102(e) Date: May 13, 1997

[87] PCT Pub. No.: WO96/09034

PCT Pub. Date: Mar. 28, 1996

[30] Foreign Application Priority Data

Sep. 21, 1994  [EP]  European Pat. Off. .............. 94202701

[51] Int. Cl.⁶ ....................................................... A61K 7/16
[52] U.S. Cl. ................................................................ 424/49
[58] Field of Search ................................................. 424/49

[56] References Cited

U.S. PATENT DOCUMENTS

| | | |
|---|---|---|
| 3,450,813 | 6/1969 | Muhler . |
| 3,538,230 | 11/1970 | Pader et al. . |
| 3,803,301 | 4/1974 | Cordon et al. . |
| 4,632,826 | 12/1986 | Ploger et al. . |
| 4,863,722 | 9/1989 | Rosenthal .................................. 424/49 |
| 5,032,383 | 7/1991 | Evans et al. ............................... 424/49 |
| 5,039,514 | 8/1991 | Evans et al. ............................... 424/52 |
| 5,108,734 | 4/1992 | Colodney et al. ......................... 424/49 |
| 5,338,524 | 8/1994 | Maurer et al. ........................... 423/409 |

FOREIGN PATENT DOCUMENTS

| | | |
|---|---|---|
| 675632 | 5/1966 | Belgium . |
| 0 170 871 | 2/1986 | European Pat. Off. . |
| 0 269 966 | 6/1988 | European Pat. Off. . |
| 0 473 171 | 3/1992 | European Pat. Off. . |
| 2183228 | 5/1973 | France . |
| 974 958 | 6/1961 | Germany . |
| 55-019235 | 2/1980 | Japan . |
| 55031 | 12/1900 | Luxembourg . |
| 2 252 042 | 7/1992 | United Kingdom . |
| 2 272 640 | 5/1994 | United Kingdom . |

*Primary Examiner*—Peter F. Kulkosky
*Attorney, Agent, or Firm*—Milton L. Honig

[57] ABSTRACT

The invention relates to oral care products such as toothpastes with an improved sensorially-perceivable cleaning benefit. This is achieved by the inclusion in the oral care products of agglomerates, substantially free from organic and/or inorganic binding agents, whereby the agglomerates are made of at least two, chemically and/or physically different particulate materials of specified particle sizes. The inclusion of materials having a therapeutic benefit on the teeth or gums in the agglomerates such as zinc citrate provides for a further benefit in that this material is slowly released from the agglomerates, thus providing for a delivery of this material over a longer period. Upon use, the gritty-feeling agglomerates will break-down into smaller particles, thus giving the consumer the feeling of initial cleaning and subsequent polishing.

12 Claims, No Drawings

ORAL COMPOSITIONS

BACKGROUND OF THE INVENTION

1. Field of the Invention

The present invention relates to oral compositions for use in the human mouth. More particularly, it relates to oral compositions which contain agglomerates of particulate materials, which agglomerates impart a sensory benefit to the oral compositions which is perceivable upon use of the oral compositions.

The present invention especially relates to oral compositions which contain agglomerated particulate materials which contain at least a particulate dental abrasive cleaning agent, imparting to the oral composition a sensorially-perceivable cleaning benefit.

2. The Related Art

Oral compositions of the above type have already been proposed in the art. Thus, in EP-A-269,966, EP-A-473,171 and GB-A-2,252,042 oral compositions have been described which contain granules which are made from particulate dental abrasive cleaning agents which have been agglomerated with the aid of organic or inorganic binding agents. Upon use of such oral compositions in the mouth, the consumer perceives the presence of these granules, giving him the sensorial perception of a cleaning efficacy, and during brushing of the teeth with these oral compositions the granules are "crushed" by the pressure of the brush, whereby they fall apart into smaller particles which deliver a polishing effect, which the consumer sensorially perceives by a smooth feel of the oral composition and of the teeth. Typical examples of such granules are made of zeolite and colloidal silica, and magnesium alumino metasilicate as the binding agent or ethylcellulose as the binding agent.

In GB-A-2,272,640 oral compositions are described with abrasive particles which are friable under conditions of use of the composition. These particles are made from a particulate dental abrasive cleaning agent such as silica, which is agglomerated without the aid of an inorganic or organic water-insoluble binding agent, but rather by treatment with water and subsequent drying.

Although these prior proposals may lead to oral compositions that can deliver a certain sensory benefit, such benefit is not quite pronounced in several aspects. Furthermore, where mixtures of different materials are agglomerated, this requires the use of an organic or inorganic binding agent, which makes the manufacture of these agglomerates more expensive.

SUMMARY OF THE INVENTION

We have now found, that agglomerates, substantially free from organic and/or inorganic binding agents, having A) a particle size such that the $D_{10}$ is equal to or bigger than 50 micrometer and the $D_{90}$ is equal to or smaller than 2000 micrometer and having a $D_{50}$ ranging from 80 micrometer to 1500 micrometer, said agglomerates being made up from at least two particulate materials, said materials being chemically and/or physically different from each other, whereby at least one particulate material has B) a particle size such that the $D_{10}$ is equal to or bigger than 0.1 micrometer and the $D_{90}$ is equal to or smaller than 80 micrometer and a $D_{50}$ ranging from 4 to 35 micrometer, and C) at least one other particulate material has a particle size such that the $D_{10}$ is equal to or bigger than 0.1 micrometer and the $D_{90}$ is equal to or smaller than 100 micrometer and a $D_{50}$ ranging from 9 to 70 micrometer, when incorporated into an oral composition yield an oral composition which delivers to the consumer a sensorially-perceivable cleaning and polishing benefit upon the use of such oral composition for brushing the teeth.

The $D_{10}$ is the particle size of no more than 10% by weight of the total amount of particles; thus, for example, a $D_{10}$ of 50 micrometers means that no more than 10% by weight of the total amount of particles may have a particle size of 50 micrometer or less. The $D_{50}$ is the particle size, 50% by weight of the total amount of particles is bigger than and 50% by weight of the total amount of particles is smaller than.

The $D_{90}$ is the particle size, 90% by weight of the total amount of the particles should be equal to or smaller than.

As to the $D_{10}$, $D_{90}$ and $D_{50}$ of A), the preferred values are:

$D_{10} \geq 100\mu$, particularly $\geq 150\mu$ $D_{90} \leq 1500\mu$, particularly $\leq 1000\mu$ $D_{50}$ from $150\mu$–$800\mu$, particularly from $200$–$600\mu$.

For B, these values are:

$D_{10} \geq 2\mu$, particularly $\geq 2.5\mu$ $D_{90} \leq 65\mu$, particularly $\leq 40\mu$ $D_{50}$ from $6\mu$–$20\mu$.

For C, these values are:

$D_{10} \geq 3\mu$, particularly $\geq 4\mu$ $D_{90} \leq 80\mu$, particularly $\leq 50\mu$ $D_{50}$ from $10\mu$–$40\mu$.

All the above particle sizes are measured using a Malvern Mastersizer model X with a MG15 sample presentation unit, using the measurement procedure outlined in the instruction manual, using a 300 micron lens in the detector system.

A more accurate measure of the true particle size distribution of the agglomerates is obtained by using sieve analysis. 100 g of the sample is placed on the top sieve of a series of BS sieves, at approximately 50 micron intervals between 45 and 600 microns. The sieves are arranged in order with the finest at the bottom and the coarsest at the top of the 5 stack. The sieves are placed in a mechanical vibrator e.g.

Inclyno Mechanical Sieve Shaker by Pascall Engineering Co Ltd., covered with a lid and shaken for 10 minutes. Each sieve fraction is accurately weighed and the results calculated:

$$\% \text{ residue} = \frac{\text{Wt. of residue} * 100}{\text{Wt. of sample}}$$

A particle size distribution can then be plotted from the data.

The amounts of the chemically and/or physically different particulate materials in the agglomerates may vary from 70–100% by weight of the agglomerates, the balance, if any, being made up by additional ingredients to be discussed hereafter. The relative weight ratio of the chemically and/or physically different particulate materials in the agglomerate may vary from 20:80 to 80:20, preferably from 25:75 to 75:25.

The particulate materials, making up the agglomerate, are chemically and/or physically different from each other. Suitable particulate materials include particulate abrasive cleaning agents such as silicas, aluminas, calcium carbonates, dicalcium phosphates, calcium pyrophosphates, hydroxy apatites, perlites, zeolites, pumice, volcanic ash, hectorites, saponites, aragonites, dolomites, talcites, hydroxytalcites, spangolites, zincites, zincosilicates, metaphosphates and mixtures of two or more of the above materials. Examples of mixtures of the particulate materials are silicas plus calcium carbonates, silicas plus dicalcium phosphate, silicas plus perlite, abrasive silicas plus thickening silicas, hydroxyapatites plus silicas or metaphosphates, calcium carbonates plus dicalcium phosphates etc.. Particularly preferred are mixtures of abrasive silicas and thickening silicas.

We have furthermore found, that the inclusion of a material having a therapeutic effect on the gums or teeth or oral cavity into these agglomerates provides for a further benefit in that upon the crushing or collapsing of these agglomerates, the therapeutic agent is slowly released, thus delivering a therapeutic efficiency of the agent over a longer period of time. Suitable examples of such therapeutic agents are zinc salts such as zinc citrate; antimicrobial agents such as Triclosan; anti-caries agents such as sodium fluoride and sodium monofluorophosphate; anti-plaque agents such as stannous pyrophosphate; anti-tartar agents such as sodium pyrophosphate and potassium pyrophosphate; anti-sensitive teeth agents such as potassium salts or strontium salts etc.

In this respect it has surprisingly been found, that the inclusion of zinc citrate in the agglomerates (in an amount of up to 25%, preferably up to 12% by weight of the agglomerates) significantly reduced the level of astringency, perceived by trained panelists upon testing a toothpaste with such agglomerates for their sensory properties.

The invention will now be further described in detail.

DETAILED DESCRIPTION OF THE INVENTION

In accordance with the invention, when an oral composition such as a toothpaste is used in the mouth with brushing, the shear and/or crush forces which are created should be sufficient to cause the particles of the agglomerates to break up after a period of time, preferably a short period of time, whereby the gritty feel experienced by the user is eliminated.

This means, that the agglomerates should have a body strength such that they collapse within the range of shear and/or crush forces normally produced in the relevant brushing regime, since the considerably variable forces produced at a particular location over time enable at least some of the agglomerates to survive intact long enough to perform their cleaning function to a satisfactory degree.

It is even possible to tailor the breakdown time of the agglomerates, such as to control the contact time for a given duration of brushing of the composition, by controlling the average crush strength of the agglomerates, for example by selecting a particular type of source of the particulate materials and/or the manner in which the agglomeration is carried out in the manufacturing process.

When the agglomerates break up under the action of shear and/or crush forces, the resulting average particle size (diameter) will typically be less than about 60 microns. Such reduced particle sizes will generally avoid any feeling of grittiness in the mouth, and impart a feeling of polished teeth.

Particularly preferred are abrasive silicas, such as low structure silicas available from Crosfield Chemicals under the trade name AC77. Mixtures of various abrasive particulate materials can also be used.

Particulate thickening agents, which may be used in the agglomerates, can be any suitable particulate thickening gent, such as clays, but preferred are thickening silicas, for example thickening silica sold under the trade mark ident 22S (ex Degussa). Other suitable silicas include for example Zeodent 165 (ex Zeofinn), Sorbosil TC 15 (ex Crosfield Chemicals), Tixosil 43 (ex Rhone-Poulenc), Sylox 15X (ex W. R. Grace).

Owing to the porous nature of the agglomerates, it is possible for them to act as delivery vehicles for various substances such as colouring pigments, opacifying agents, flavours, perfumes or other cosmetic or, as said before, therapeutic dental and/or oral actives e.g. fluoride compounds, antibacterial agents such as Triclosan and zinc salts such as zinc citrate, anti-caries agents, anti-tartar agents, anti-sensitive teeth agents etc.. Such substances may be contained within the pores of the material (e.g. introduced therein by conventional techniques) and, as the particles break up during use of the composition, released therefrom when the composition is used in the mouth, e.g. upon brushing.

Suitable industrial process for forming the agglomerates such as described above include: spray drying a mixture of the particulate materials wetted with a suitable amount of a volatile liquid such as water; granulation, of a similar nature to that used in the preparation of solid detergents in granular form; and pressure compaction. Such processes are well known in the art.

In the oral compositions according to the present invention, the level of the agglomerates may be wide ranging, for example depending upon the physical form of the desired end product.

Compositions according to the invention may be solids, e.g. similar in form to conventional tooth powders, or pastes, creams or gels, e.g. like conventional toothpastes, or possibly even liquids.

Particularly preferred compositions of the invention are in the form of pastes, gels, creams or liquids, the exact physical properties of which may be controlled for example by suitable adjustment of the solid to liquid ratio and/or the viscosity of the liquid phase, e.g. by selecting appropriate contents of adjunct components, as described further below.

In the particularly preferred compositions of the invention the agglomerates should be insoluble in the medium of the composition into which they are incorporated. In this context, "insoluble" means having sufficient insolubility at ambient temperature that the agglomerates remain undissolved or substantially undissolved in the composition such that their friability under the conditions of use of the composition and thus their ability to perform their cleaning/ polishing function are not deleteriously affected. Preferably, the level of insolubility of the agglomerates extend to its insolubility in the oral environment in which the composition is used, which may frequently contain higher levels of water than for example a toothpaste, owing to the present of saliva and added water frequently used in the brushing regime.

In preferred embodiments of the invention, the agglomerates are present in the composition in an amount of from about 1 to about 99% by weight, more preferably from about 2 to about 60%, even more preferably from about 3 to about 40%. In liquid compositions the latter preferred range is particularly suitable. In paste compositions of the invention, the agglomerates are preferably present in an amount of from about 1 to about 25% by weight, more preferably from about 1 to about 15%, even more preferably from about 2 to about 10%.

The oral compositions of the invention may contain one or more additional components, as will now be described.

Oral compositions of the invention preferably comprise one or more surfactants, preferably selected from anionic, nonionic, amphoteric and zwitterionic surfactants, and mixtures thereof, all being suitable for dental and/or oral use.

Suitable anionic surfactants may include soaps, alkyl sulphates, alkyl ether sulphates, alkaryl sulphonates, alkanoyl isethionates, alkanoyl taurates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Example of preferred anionic surfactants may include sodium lauryl sulphate, sodium dodecylbenzene sulphonate, sodium lauroyl sarcosinate and sodium coconut monoglyceride sulphonate.

Nonionic surfactants which may be suitable for use in composition of the invention include sorbitan and polyglycerol esters of fatty acids, as well as ethylene oxide/propylene oxide block copolymers.

Amphoteric surfactants which may be suitable for use in compositions of the invention include betaines such as cocamidopropyl betaine, and sulphobetaines, for example.

The surfactant(s) may be present in the oral composition of the invention in a total amount of from about 0.1 to about 3% by weight.

Water is another preferred component of the oral compositions of the invention and may be present in an amount of from about 1 to about 90% by weight, preferably from about 10 to about 60%, more preferably from about 15 to about 50%.

Toothpastes and creams of this invention may also contain humectants, for example polyols such as glycerol, sorbitol syrup, polyethylene glycol, lactitol, xylitol and hydrogenated corn syrup. The total amount of humectant, if present, may be for example in the range of from about 10 to about 85% by weight of the composition.

In the oral compositions of the present invention it is particularly preferred that one or more thickening agents and/or suspending agents are included, in order to give the composition the desired physical properties (e.g. whether a paste, cream or a liquid) and in order that the agglomerates remain stably dispersed throughout the composition.

A particularly preferred means for thickening the oral compositions of the invention is by the inclusion of conventional thickening materials such as thickening silicas, examples of which have already been mentioned above.

Other suitable suspending/thickening agents are well known in the art and include for example polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof), heteropolysaccharide gums, and cellulose derivatives such as sodium carboxymethyl cellulose.

Particularly suitable thickening agents are heteropolysaccharide gums such as xanthan gum and guar gums.

The thickening agent and/or suspending agent (which may be used singly or as mixtures of two or more such materials) may be present in the composition in a total amount of from about 0.1 to about 50% by weight; preferably from about 5 to about 15% for silica thickening agents; preferably from about 0.1 to about 5% for polymer suspending agents.

The compositions of the invention may contain one or more other components conventionally found in oral compositions. Suitable additional ingredients include: flavouring substances, e.g. peppermint, spearmint; artificial sweeteners; perfume or breath freshening substances; pearlescing agents; peroxy compounds, e.g. hydrogen peroxide or peracetic acid; opacifiers; pigments and colourings; preservatives; moisturising agents; fluoride-containing compounds; anti-caries agents; anti-plaque agents; therapeutic agents such as zinc citrate, Triclosan (ex Ciba Geigy); proteins; salts; pH adjusting agents. Furthermore, the compositions usually comprise additional abrasive cleaning agents in amount of 5–60% by weight, such as abrasive silicas, chalks, hydrated aluminas, calcium phosphate, calcium pyrophosphates, hydroxy apatites, insoluble metaphsophates; etc.

Compositions in accordance with the present invention may be made by conventional methods of preparing oral compositions. Pastes and creams may be prepared by conventional techniques using high shear mixing systems under vacuum, for example, with the agglomerates which characterise the invention being added to the pre-mixed base composition in a secondary step comprising dispersing/mixing in thereof under low shear conditions.

It is generally important in the preparation of compositions in accordance with the invention that any mixing step carried out is done at a sufficiently low shear and/or speed such that the agglomerates of the invention do not experience forces sufficiently great to cause the particles to fracture.

The oral compositions of the invention may be used in a similar way to conventional oral compositions such as toothpastes, i.e. a suitable amount of the composition is applied to a brush, or even directly into the mouth, if necessary with the addition of some water, and the slurry worked on the teeth, gums and/or other mouth parts as necessary or desired, so as to exert the properties of the agglomerates onto the intended intraoral surfaces. Owing to the friability of the agglomerates, any grittiness experienced by the user will soon disappear, so that once the agglomerates have performed their cleaning function, the composition is left free for further polishing or for example for delivering one or more additional benefits attributable to other components in the composition. Finally, the mouth may be rinsed with water, as with normal oral products, This applications procedure may be repeated as many times as desired.

The invention is further illustrated by the following Examples.

EXAMPLE 1

The following particulate silica materials were blended together and mixed with zinc citrate trihydrate and/or titanium dioxide to give an intimate mixture:

|  | 1<br>Parts by<br>Weight | 2<br>Parts by<br>Weight |
| --- | --- | --- |
| Sorbosil AC77 (*) | 43.15 | 48.5 |
| Sorbosil TC15 (*) | 43.15 | 48.5 |
| Titanium Dioxide | 3.0 | 3.0 |
| Zinc citrate trihydrate | 10.7 | 0.0 |

The silicas had the following properties:

|  | Sorbosil AC77 | Sorbosil TC15 |
| --- | --- | --- |
| Surface Area $m^2/g$ | 120 | 260 |
| av. $D_{10}$ | 2.7 | 5.6 |
| av. $D_{50}$ | 8.1 | 12.9 |
| av. $D_{90}$ | 17.8 | 29.3 |

(*) - obtainable from Joseph Crosfield & Sons - England.

Water was added to this mixture to give a water:solids ratio of 1.33 to 1, the resulting blend being granulated in a pan granulator.

The resulting wet agglomerates were then either dried for 4 hours in an oven at 120° C. or partially dried for 30 minutes in a fluid bed drier and finished in an oven for 2 hours at the same temperatures as above. The particle size distribution was adjusted by screening at 150 and 400 microns.

The weight mean particle size of the silicas and agglomerates was determined using a Malvern Mastersizer model X with MS15 sample presentation unit. The silicas were dispersed ultrasonically and the agglomerates mechanically stirred before they were subjected to the measurement procedure outlined in the instruction manual for the instrument utilising a 300 micron lens in the detector system.

After determining the weight mean particle size distribution of the agglomerates, as described above, a further sample of the agglomerates was dispersed using ultrasonics for two minutes, setting 100, and subjected to the measurement procedure. The $D_{10}$, $D_{50}$ and $D_{90}$ could then be interpolated from the particle size distribution, and the higher the values obtained after the exposure to ultrasonics the stronger the agglomerates.

The following results were obtained:

|  | Ultrasonics | $D_{10}$ | $D_{50}$ | $D_{90}$ |
| --- | --- | --- | --- | --- |
| Composition 1 | 0 | 193 | 334 | 502 |
|  | 100 | 3.3 | 14.3 | 42 |
| Composition 2 | 0 | 268 | 391 | 539 |
|  | 100 | 3.3 | 12 | 39 |

A toothpaste was prepared with the agglomerates of composition 1, said toothpaste having the following formulation:

| INGREDIENTS | % W/W |
| --- | --- |
| Sorbitol syrup 70% | 45.00 |
| Sodium fluoride | 0.32 |
| Saccharin | 0.20 |
| Titanium dioxide | 0.10 |
| Polyethyleneglycol (MW1500) | 5.00 |
| Blue N° 1 | 0.0003 |
| Abrasive Silica (AC77) | 8.00 |
| Thickener Silica (TC15) | 7.00 |
| Cellulose Gum (CMC9) | 0.80 |
| Sodium laurylsulphate | 1.80 |
| Flavour | 1.20 |
| Agglomerates of composition 1 | 7.00 |
| Water | To 100 |

This formulation (A) was submitted to a qualitative descriptor analysis test using trained panelists, in which test for comparison purposes the formulation was compared to a formulation (B) with zeolite-agglomerates according to EP 269,966.

This following results were obtained (using a scale of 0–10):

|  | Visibility | Hardness | Ease of Breaking |
| --- | --- | --- | --- |
| Formulation A | 5.5 | 3.7 | 7.7 |
| Formulation B | 6.0 | 4.0 | 7.0 |

If the ratio of TC15 to AC77 in the agglomerates of composition 1 was changed to 75:25 (C), the following data were obtained:

|  | Visibility | Hardness | Ease of Breaking |
| --- | --- | --- | --- |
| Formulation C | 4.1 | 4.2 | 6.8 |

EXAMPLE 2

Repeating Example 1, but using the agglomerates of composition 2, gave the following results:

|  | Visibility | Hardness | Ease of Breaking |
| --- | --- | --- | --- |
| Formulation $A^1$ | 7.1 | 6.5 | 5.1 |
| Formulation $B^1$ | 6.0 | 4.0 | 7.0 |

If the ratio of TC15 to AC77 in the agglomerates of composition 2 was changed to 25:75 (D), the following data were obtained:

|  | Visibility | Hardness | Ease of Breaking |
| --- | --- | --- | --- |
| Formulation D | 4.1 | 5.1 | 6.4 |

EXAMPLE 3

The agglomerates of composition 1 were tested as to the retention of the zinc citrate in the agglomerates. The agglomerates were slurried into water (Example 1) and into a sorbitol/water mixture (Example 2), and the amount of zinc ions, released into the water or sorbitol/water mixture was determined at various intervals. The following results were obtained:

|  | % Zn Solubility | | | |
|---|---|---|---|---|
| time (mins) | 60 | 480 | 1440 | 2880 |
| Example 1 | 36.57 | 35.45 | 36.29 | 34.94 |
| Example 2 | 12.24 | 12.25 | 13.47 | 13.29 |

The release of the zinc from the agglomerates upon brushing was also measured using a brushing machine. It was found that after 2 minutes brushing 60% of the available zinc was released when using a smooth surface, and 70% when using a gritty surface.

EXAMPLE 4

A comparison between a zinc citrate containing commercial toothpaste, Mentadent P, and formulation A was made using a qualitative description analysis test with trained panelists as to the astringency of the products. With Mentadent P, a value of 7.6 was obtained, and with formulation A a value of 4.0.

EXAMPLE 5

Series of various agglomerates were prepared and tested in toothpaste formulation A or B for their sensory properties by a panel of three people.

The toothpaste formulation A was as follows;

|  | % by weight |
|---|---|
| sorbitol (70%) | 45 |
| saccharin | 0.2 |
| sodium fluoride | 0.32 |
| titanium dioxide | 0.1 |
| polyethyleneglycol (MW 1500) | 5 |
| Blue no. 1 | 0.0005 |
| abrasive silica | 8 |
| thickening silica | 7 |
| carboxymethylcellulose (CMC9) | 0.8 |
| sodium laurylsulphate | 1.8 |
| flavour | 1 |
| agglomerates | 7 |
| water | to 100 |

The toothpaste formulation B was as follows:

|  | % by weight |
|---|---|
| glycerol | 35 |
| saccharin | 0.27 |
| sodium fluoride | 0.32 |
| titanium dioxide | 1 |
| polyethyleneglycol (MW 1500) | 5 |
| abrasive silica | 8 |
| thickening silica | 7 |
| sodium bicarbonate | 10 |
| carboxymethylcellulose (CMC() | 0.7 |
| sodium laurylsulphate | 1.8 |
| flavour | 1.5 |
| agglomerates | 7 |
| water | to 100 |

The agglomerates all had a particle size distribution within the range of 150 to 400 microns, and the particulate materials from which the agglomerates were made all had a particle size distribution within the ranges as specified in the present application.

|  | % by weight | | | | | | | | | | |
|---|---|---|---|---|---|---|---|---|---|---|---|
|  | No. | | | | | | | | | | |
|  | 1 | 2 | 3 | 4 | 5 | 6 | 7 | 8 | 9 | 10 | 11 |
| calcium carbonate | 50 | 50 | 50 | 45 | 45 | 45 | 50 | 45 | 100 | 67 | 57 |
| dicalciumphosphate | 50 | — | — | 45 | — | — | — | — | — | — | — |
| thickening silica | — | 25 | — | — | 22.5 | — | — | — | — | — | — |
| abrasive silica | — | 25 | — | — | 22.5 | — | — | — | — | — | — |
| perlite | — | — | 50 | — | — | — | — | — | — | — | — |
| sodium bicarbonate | — | — | — | — | — | — | 50 | 45 | — | — | — |
| zinc citrate | — | — | — | 10 | 10 | — | — | 10 | — | — | 10 |
| calcium pyrophosphate | — | — | — | — | — | — | — | — | — | 33 | 33 |

|  | % by weight | | | | | | | | | | |
|---|---|---|---|---|---|---|---|---|---|---|---|
|  | No. | | | | | | | | | | |
|  | 12 | 13 | 14 | 15 | 16 | 17 | 18 | 19 | 20 | 21 | 22 |
| calcium carbonate | — | — | — | — | — | — | — | — | — | — | — |
| dicalciumphosphate | 50 | 50 | 45 | — | — | 67 | 45 | — | — | 33 | 30 |
| thickening silica | 25 | — | 22.5 | 25 | 22 | — | — | — | — | 17 | 15 |
| abrasive silica | 25 | — | 22.5 | 25 | 22 | — | — | — | — | 17 | 15 |
| perlite | — | 50 | — | — | — | — | 45 | 50 | 45 | — | — |
| sodium bicarbonate | — | — | — | 50 | 46 | — | — | — | — | 33 | 30 |
| zinc citrate | — | — | 10 | — | 10 | — | 10 | — | 10 | — | 10 |
| calcium pyrophosphate | — | — | — | — | — | 33 | — | 50 | 45 | — | — |

The results of the sensory property tests were as follows:

| Agglomerate | Toothpaste | Perception of particles | Mouthfeel in use |
|---|---|---|---|
| 1 | B | very well | good |
| 2 | B | well | good |
| 3 | B | hardly | poor |
| 4 | B | very well | good |
| 5 | B | well | good |
| 6 | B | hardly | poor |
| 7 | B | hardly | poor |
| 8 | B | very well | good |
| 9 | B | very well | good |
| 10 | A | very well | good |
| 11 | A | hardly | poor |
| 12 | A | very well | good |
| 13 | A | very well | gritty |
| 14 | A | very well | little gritty |
| 15 | B | very well | good |
| 16 | B | very well | good |
| 17 | A | very well | gritty |
| 18 | A | very well | gritty |
| 19 | A | very well | gritty |
| 20 | A | very well | good |
| 21 | A | very well | gritty |
| 22 | A | very well | gritty |

The following agglomerates, prepared by a dry compacting route, were also tested in toothpaste formulation A, and they could be perceived very well with a good mouthfeel.

The agglomerates had a particle size distribution of between 150 and 400 microns, and the particle materials from which the agglomerates were made had a particle size distribution within the ranges as specified in the present application.

The agglomerates had the following compositions:

| No. | 1 | 2 | 3 | 4 | 5 | 6 | 7 | 8 |
|---|---|---|---|---|---|---|---|---|
| abrasive silica | 10.3 | 23.81 | 26.3 | 23.3 | 27.65 | 24.5 | 36 | 41 |
| thickening silica | 10.3 | 23.81 | 26.3 | 23.3 | 27.65 | 24.5 | 36 | 41 |
| titanium dioxide | 3.0 | 3.0 | 3.0 | 3.0 | 3.0 | 3.9 | 3.0 | 3.0 |
| potassium | 76.4 | 43.3 | — | — | — | — | — | — |
| zinc citrate | — | 6.08 | — | 5.95 | — | 6.25 | 10.71 | 10.7 |
| tetra potassium pyrophosphate | — | — | 24.6 | 24.6 | — | — | — | — |
| tetrasodium pyrophosphate | — | — | 19.8 | 19.8 | — | — | — | — |
| potassium nitrate | — | — | — | — | 41.7 | 41.7 | — | — |
| stannous pyrophosphate | — | — | — | — | — | — | 14.29 | — |
| Triclosan | — | — | — | — | — | — | — | 4.3 |

I claim:

1. An oral composition comprising agglomerates of particulate materials characterised in that the agglomerates are substantially free from organic and/or inorganic binding agents, said agglomerates having A) a particle size such that the $D_{10}$ is equal to or bigger than 50 micrometer and the $D_{90}$ is equal to or smaller than 2000 micrometer and having a $D_{50}$ ranging from 80 micrometer to 1500 micrometer, said agglomerates being made up from at least two particulate materials in a relative weight ratio from 20:80 to 80:20, said materials being chemically and/or physically different from each other, whereby at least one particulate material has B) a particle size such that the $D_{10}$ is equal to or bigger than 0.1 micrometer and the $D_{90}$ is equal to or smaller than 80 micrometer and a $D_{50}$ ranging from 4 to 35 micrometer, and C) at least one other particulate material has a particle size such that the $D_{10}$ is equal to or bigger than 0.1 micrometer and the $D_{90}$ is equal to or smaller than 100 micrometer and a $D_{50}$ ranging from 9 to 70 micrometer, and upon use the gritty-feeling agglomerates will break-down into smaller particles, thus giving a consumer a feeling of initial cleaning and subsequent polishing.

2. A composition according to claim 1, characterised in that for A), the $D_{10} \geq 100\mu$, the $D_{90} \leq 1500\mu$ and the $D_{50}$ is from 150–800$\mu$, for B) the $D_{10} \geq 2\mu$, the $D_{90} \leq 65\mu$, and the $D_{50}$ is from 6–20$\mu$, and for C) $D_{10} \geq 3\mu$, the $D_{90} \leq 80\mu$, and the $D_{50}$ is from 10–40$\mu$.

3. A composition according to claim 2, characterised in that for A) the $D_{10} \geq 150\mu$, the $D_{90} \leq 1000\mu$ and the $D_{50}$ is from 200–600$\mu$, for B) the $D_{10} \geq 2.5\mu$, the $D_{90} \leq 40\mu$ and for C) the $D_{10} \geq 4\mu$, the $D_{90} \leq 50\mu$.

4. A composition according to claim 1, characterised in that the agglomerates consist of at least 70 % by weight of the particulate materials.

5. A composition according to claim 1, characterised in that the agglomerates further contain a material having a cosmetic or therapeutic dental benefit.

6. A composition according to claim 5, characterised in that the agglomerates contain a zinc compound.

7. A composition according to claim 1, characterised in that it contains the agglomerates in an amount of 1–99% by weight.

8. A composition according to claim 7, characterised in that it contains the agglomerates in an amount of 3 to 40% by weight.

9. A composition according to claim 1, characterised in that the agglomerates are made of a mixture of thickening and abrasive silicas in a relative weight ratio of 75:25 to 25:75.

10. A composition according to claim 9, characterised in that the agglomerates comprise a thickening and an abrasive silica in a relative weight ratio of 50:50 and furthermore comprise titanium dioxide and zinc citrate.

11. A composition according to claim 1 wherein the agglomerates are present in an amount from about 2 to about 60% by weight.

12. A composition according to claim 1 wherein the agglomerates are present in an amount from about 1 to about 25% by weight.

* * * * *